(12) United States Patent
Kwok (10) Patent No.: US 6,494,207 B1
(45) Date of Patent: *Dec. 17, 2002

(54) HARNESS ASSEMBLY FOR A NASAL MASK

(75) Inventor: Philip Rodney Kwok, West Pymble (AU)

(73) Assignee: ResMed Limited, North Ryde (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/982,755

(22) Filed: Dec. 2, 1997

(30) Foreign Application Priority Data

Dec. 2, 1996 (AU) ................................................ PO3995

(51) Int. Cl.$^7$ ................................................ A62B 18/08
(52) U.S. Cl. ............................. 128/207.11; 128/207.13; 128/206.27; 2/452
(58) Field of Search .................. 128/207.11, 207.13, 128/205.25, 206.12, 206.21, 206.24, 206.26, 206.27; 2/9, 181.2, 174, 426, 427, 428, 429, 430, 452

(56) References Cited

U.S. PATENT DOCUMENTS

| | | | |
|---|---|---|---|
| 781,516 A | 1/1905 | Guthrie | |
| 812,706 A | 2/1906 | Warbasse | |
| 1,081,745 A | 12/1913 | Johnston et al. | |
| 1,192,186 A | 7/1916 | Greene | |
| 1,653,572 A | 12/1927 | Jackson | |
| 1,926,027 A | 9/1933 | Biggs | |
| 2,123,353 A | 7/1938 | Catt | |
| 2,248,477 A | 7/1941 | Lombard | |
| 2,254,854 A | 9/1941 | O'Connell | |
| 2,317,608 A | * 4/1943 | Mask | 128/206.24 |
| 2,371,965 A | 3/1945 | Lehmberg | |
| 2,376,871 A | 5/1945 | Fink | |
| 2,415,846 A | 2/1947 | Randall | |
| 2,438,058 A | 3/1948 | Kincheloe | |
| 2,578,621 A | 12/1951 | Yant | |
| 2,931,356 A | 4/1960 | Schwarz | |
| D188,084 S | 5/1960 | Garelick | |
| 2,939,458 A | 6/1960 | Lundquist | |
| 3,013,556 A | * 12/1961 | Galleher, Jr. | 128/207.11 |
| 3,182,659 A | 5/1965 | Blount et al. | |
| 3,189,027 A | 6/1965 | Bartlett | |
| 3,193,624 A | 7/1965 | Webb et al. | |

(List continued on next page.)

FOREIGN PATENT DOCUMENTS

| | | |
|---|---|---|
| AU | 91/77110 B | 11/1991 |
| AU | 94/64816 B | 12/1994 |
| AU | 95/16178 B | 7/1995 |

(List continued on next page.)

OTHER PUBLICATIONS

Mask 1 Photographs, Respironics Inc., Reusable Full Mask (small) Part # 452033 Lot #951108.

(List continued on next page.)

*Primary Examiner*—John G. Weiss
*Assistant Examiner*—Joseph F. Weiss, Jr.
(74) *Attorney, Agent, or Firm*—Pillsbury Winthrop LLP (57) ABSTRACT

A harness assembly (40) for a nasal mask (42) for communicating breathable gas to a patient's airways, for example in the administering CPAP or like breathable gas delivery treatments. The harness assembly (40) includes a cap portion (44) adapted to engage, in use, the occipital region of the skull (43). In one form, the cap portion (44) includes a D-shaped coupling (48) at each end and the harness assembly (40) includes a pair of upper (52) and lower (54) straps, each of the straps (52, 54) extending between one of the D-shaped couplings (48) and the nasal mask (42). The harness assembly (40) grips the head (43) in a region substantially fixed relative to the face and, as such, tension of the straps (52, 54) is not substantially affected by head movement. Couplings of other shapes are also discussed.

25 Claims, 7 Drawing Sheets

U.S. PATENT DOCUMENTS

| | | | |
|---|---|---|---|
| 3,238,943 A | | 3/1966 | Holley |
| 3,315,674 A | * | 4/1967 | Bloom et al. .......... 128/206.12 |
| 3,330,273 A | | 7/1967 | Bennett |
| 3,362,420 A | | 1/1968 | Blackburn et al. |
| 3,363,833 A | | 1/1968 | Laerdal |
| 3,556,122 A | | 1/1971 | Laerdal |
| 3,580,051 A | | 5/1971 | Blevins |
| 3,700,000 A | | 10/1972 | Hesse |
| 3,720,235 A | | 3/1973 | Schrock |
| 3,796,216 A | | 3/1974 | Schwarz |
| 3,799,164 A | | 3/1974 | Rollins |
| D231,803 S | | 6/1974 | Huddy |
| 4,077,404 A | | 3/1978 | Elam |
| D250,131 S | | 10/1978 | Lewis et al. |
| 4,167,185 A | | 9/1979 | Lewis |
| 4,226,234 A | | 10/1980 | Gunderson |
| 4,245,632 A | | 1/1981 | Houston |
| D262,322 S | | 12/1981 | Mizerak |
| 4,304,229 A | | 12/1981 | Curtin |
| 4,328,797 A | | 5/1982 | Rollins, III et al. |
| 4,347,205 A | | 8/1982 | Stewart |
| 4,354,488 A | | 10/1982 | Bartos |
| 4,402,316 A | * | 9/1983 | Gadberry ............... 128/201.15 |
| 4,412,537 A | | 11/1983 | Tiger |
| 4,467,799 A | | 8/1984 | Steinberg |
| 4,522,639 A | | 6/1985 | Ansite et al. |
| 4,558,710 A | | 12/1985 | Eichler |
| 4,616,647 A | * | 10/1986 | McCreadie ............ 128/206.19 |
| 4,622,964 A | | 11/1986 | Flynn |
| 4,655,213 A | | 4/1987 | Rapoport et al. |
| 4,665,570 A | | 5/1987 | Davis |
| 4,671,271 A | | 6/1987 | Bishop et al. |
| 4,677,975 A | | 7/1987 | Edgar et al. |
| 4,677,977 A | | 7/1987 | Wilcox |
| D293,613 S | | 1/1988 | Wingler |
| 4,739,755 A | | 4/1988 | White et al. |
| 4,770,169 A | | 9/1988 | Schmoegner et al. |
| 4,774,941 A | | 10/1988 | Cook |
| 4,782,832 A | | 11/1988 | Trimble et al. |
| 4,799,477 A | | 1/1989 | Lewis |
| 4,809,692 A | | 3/1989 | Nowacki et al. |
| 4,819,629 A | | 4/1989 | Jonson |
| 4,821,713 A | | 4/1989 | Bauman |
| 4,841,953 A | | 6/1989 | Dodrill |
| 4,848,334 A | | 7/1989 | Bellm |
| 4,848,366 A | | 7/1989 | Aita et al. |
| 4,907,584 A | | 3/1990 | McGinnis |
| 4,910,806 A | * | 3/1990 | Baker et al. .................... 2/452 |
| 4,919,128 A | | 4/1990 | Kopala et al. |
| 4,938,210 A | | 7/1990 | Shene |
| 4,938,212 A | | 7/1990 | Gnook et al. |
| 4,944,310 A | | 7/1990 | Sullivan |
| D310,431 S | | 9/1990 | Bellm |
| 4,971,051 A | | 11/1990 | Toffolon |
| 4,986,269 A | | 1/1991 | Hakkinen |
| 4,989,596 A | | 2/1991 | Macris et al. |
| 4,989,599 A | | 2/1991 | Carter |
| 5,005,568 A | | 4/1991 | Loescher et al. |
| 5,005,571 A | | 4/1991 | Dietz |
| 5,038,776 A | | 8/1991 | Harrison et al. |
| 5,042,473 A | | 8/1991 | Lewis |
| 5,042,478 A | | 8/1991 | Kopala et al. |
| 5,046,200 A | * | 9/1991 | Feder ............................ 2/452 |
| 5,063,922 A | | 11/1991 | Hakkinen |
| 5,069,205 A | | 12/1991 | Urso |
| D323,908 S | | 2/1992 | Hollister et al. |
| 5,086,768 A | * | 2/1992 | Niemeyer ............... 128/205.24 |
| 5,109,839 A | | 5/1992 | Blasdell et al. |
| 5,109,840 A | | 5/1992 | Daleiden |
| 5,121,745 A | | 6/1992 | Israel |
| 5,133,347 A | | 7/1992 | Huennebeck |
| 5,140,980 A | | 8/1992 | Haughey et al. |
| 5,140,982 A | | 8/1992 | Bauman |
| 5,159,938 A | | 11/1992 | Laughlin |
| 5,178,138 A | | 1/1993 | Walstrom et al. |
| D334,633 S | | 4/1993 | Rudolph |
| 5,231,983 A | | 8/1993 | Matson et al. |
| 5,233,978 A | | 8/1993 | Callaway |
| 5,243,971 A | | 9/1993 | Sullivan et al. |
| 5,265,595 A | | 11/1993 | Rudolph |
| 5,279,289 A | | 1/1994 | Kirk |
| 5,280,784 A | | 1/1994 | Kohler |
| 5,311,862 A | | 5/1994 | Blasdell et al. |
| 5,322,057 A | | 6/1994 | Raabe et al. |
| 5,343,878 A | | 9/1994 | Scarberry et al. |
| 5,357,951 A | | 10/1994 | Ratner |
| 5,372,130 A | * | 12/1994 | Stern et al. ............ 128/205.25 |
| 5,388,571 A | | 2/1995 | Roberts et al. |
| 5,404,871 A | | 4/1995 | Goodman et al. |
| 5,419,318 A | | 5/1995 | Tayebi |
| 5,429,126 A | | 7/1995 | Bracken |
| 5,429,683 A | | 7/1995 | Le Mitouard |
| 5,431,158 A | | 7/1995 | Tirotta |
| 5,438,981 A | | 8/1995 | Starr et al. |
| 5,441,046 A | | 8/1995 | Starr et al. |
| D362,061 S | | 9/1995 | McGinnis et al. |
| 5,477,852 A | | 12/1995 | Landis et al. |
| 5,479,920 A | | 1/1996 | Piper et al. |
| 5,488,948 A | | 2/1996 | Dubruille et al. |
| 5,492,116 A | | 2/1996 | Scarberry et al. |
| 5,501,214 A | | 3/1996 | Sabo |
| 5,509,404 A | | 4/1996 | Lloyd |
| 5,517,986 A | | 5/1996 | Starr et al. |
| 5,538,000 A | | 7/1996 | Rudolph |
| 5,540,223 A | | 7/1996 | Starr et al. |
| 5,542,128 A | | 8/1996 | Lomas |
| 5,546,936 A | | 8/1996 | Virag et al. |
| RE35,339 E | | 10/1996 | Rapoport |
| 5,560,354 A | | 10/1996 | Berthon-Jones et al. |
| 5,570,682 A | | 11/1996 | Johnson |
| 5,570,689 A | | 11/1996 | Starr et al. |
| D377,089 S | | 12/1996 | Starr et al. |
| 5,592,938 A | | 1/1997 | Scarberry et al. |
| 5,608,647 A | | 3/1997 | Rubsamen et al. |
| 5,642,730 A | | 7/1997 | Baran |
| 5,647,355 A | | 7/1997 | Starr et al. |
| 5,647,357 A | | 7/1997 | Barnett et al. |
| 5,649,532 A | | 7/1997 | Griffiths |
| 5,649,533 A | | 7/1997 | Oren |
| 5,655,520 A | | 8/1997 | Howe et al. |
| 5,655,527 A | | 8/1997 | Scarberry et al. |
| 5,657,493 A | * | 8/1997 | Ferrero et al. .................. 2/428 |
| 5,657,752 A | | 8/1997 | Landis et al. |
| 5,662,101 A | * | 9/1997 | Ogden et al. .......... 128/205.25 |
| 5,666,946 A | | 9/1997 | Langenback |
| 5,685,296 A | | 11/1997 | Zdrojkowski et al. |
| 5,687,715 A | | 11/1997 | Landis et al. |
| 5,715,814 A | | 2/1998 | Ebers |
| 5,921,239 A | * | 7/1999 | McCall et al. ......... 128/205.25 |
| 6,044,844 A | * | 4/2000 | Kwok et al. ............ 128/207.11 |
| 6,119,692 A | * | 9/2000 | Byram ................. 128/206.27 |
| 6,192,886 B1 | * | 2/2001 | Rudolph ................ 128/207.13 |

FOREIGN PATENT DOCUMENTS

| | | |
|---|---|---|
| AU | A 32914/95 | 2/1996 |
| AU | 9459430 | 2/1996 |
| DE | 459104 | 4/1928 |
| DE | 701690 | 1/1941 |
| DE | 159396 | 6/1981 |
| DE | 3015279 A1 | 10/1981 |
| DE | 3345067 A1 | 6/1984 |

| | | | |
|---|---|---|---|
| DE | 3537507 | A1 | 4/1987 |
| DE | 3539073 | A1 | 5/1987 |
| DE | 4004157 | C1 | 4/1991 |
| DE | 4343205 | A1 | 6/1995 |
| EP | 0 054 154 | | 6/1982 |
| EP | 0 252 052 | A1 | 1/1988 |
| EP | 0 264 772 | A1 | 4/1988 |
| EP | 0 386 605 | A1 | 9/1990 |
| EP | 0427474 | A2 | 5/1991 |
| EP | 0 462 701 | A1 | 12/1991 |
| EP | 0 602 424 | | 11/1993 |
| EP | 0 608 684 | A1 | 8/1994 |
| EP | 0 697 225 | | 7/1995 |
| EP | 178 925 | A2 | 4/1996 |
| EP | 0 747 078 | A2 | 12/1996 |
| FR | 2 574 657 | A1 | 6/1986 |
| FR | 2 658 725 | A1 | 8/1991 |
| GB | 1 467 828 | | 3/1977 |
| GB | 2145335 | A | 3/1985 |
| GB | 2147506 | A | 5/1985 |
| GB | 2 164 569 | A | 3/1986 |
| JP | 09/216240 | A | 8/1997 |
| WO | WO 80/01044 | | 5/1980 |
| WO | WO 82/03548 | | 10/1982 |
| WO | WO 86/06969 | | 12/1986 |
| WO | WO 91/03277 | | 3/1991 |
| WO | WO 92/20395 | | 11/1992 |
| WO | WO 93/01854 | | 2/1993 |
| WO | WO 94/02190 | | 2/1994 |
| WO | WO 94/20051 | | 9/1994 |
| WO | WO 95/02428 | | 1/1995 |
| WO | WO 96/17643 | | 6/1996 |
| WO | WO 96/25983 | | 8/1996 |
| WO | WO 96/39206 | | 12/1996 |
| WO | WO 97/07847 | | 3/1997 |
| WO | WO 97/41911 | | 11/1997 |

OTHER PUBLICATIONS

Mask 2 Photographs, Puritan—Bennett, Adam Curcuit, Shell Part # 231700, Swivel Part #616329–00, Pillows (medium) Part # 616324.

Mask 3, Photographs, DeVilbiss Healthcare Inc., DeVilbiss Seal–Ring and CPAP Mask Kit (medium), Part 73510–669.

Mask 4 Photographs, Respironics Inc., Monarch Mini Mask with Pressure Port. Part # 572004, Monarch Headgear, Part # 572011.

Mask 5 Photographs, Healthdyne Technologies, Nasal CPAP Mask (medium narrow), Part # 702510.

Mask 6 Photographs, Healthdyne Technologies, Soft Series Nasal CPAP Mask, Part # 702020.

Mask 7 Photographs, DeVilbiss Healthcare Inc., Small Mask and Seal Rings, Part # 73510–668.

Mask 8 Photographs, Respironics Inc., Reusable Contour Mask (medium), Part # 302180.

Mask 9 Photographs, Healthdyne Technologies, Healthdyne Large Headgear.

Mask 10 Photographs, Respironics Inc., Soft Cap (medium), Part # 302142.

Mask 11 Photographs, Weinmann: Hamburg, Nasalmaskensystem mit Schalldämpfer (medium), Part # WN 23105.

Mask 12 Photographs, Life Care.

Mask 13 Photographs, Healthdyne Technologies.

Mask 14 Photographs, King System.

Mask 15 Photographs, Respironics Inc., Paediatric Mask.

Mask 16 Photographs, Hans Rudolph Inc., Hans Rudolph Silicone Rubber Face Mask/8900.

* cited by examiner

HARNESS ASSEMBLY FOR A NASAL MASK

FIELD OF THE INVENTION

This invention relates to a harness assembly for a nasal mask.

The invention will be described with reference to a harness assembly for a nasal mask fitted to the head of a wearer for communicating breathable gas to a patient's airways, for example in the administering of continuous positive airway pressure (CPAP) treatment. However, the invention is not limited to this particular field of use and is equally suited for masks used in assisted respiration or mechanical ventilation.

BACKGROUND OF THE INVENTION

CPAP treatment is administered when a person is asleep It is therefore crucial that nasal CPAP masks be securely fastened to the wearer's head. Leaks occurring due to mask movement caused by gross body motion during sleep can result in the efficacy of CPAP treatment being defeated. An effective seal of the mask cushion to the patient's face is, in part, a function of the mask design, and is also a function of the correct tension in the harness being maintained. Under-tensioning results in a loose mask and poor seal. Over-tensioning can lead to discomfort for the wearer. All of these problems can lead to patient non-compliance.

A prior art nasal mask and harness arrangement is taught in U.S. Pat. No. 5,243,971 assigned to the University of Sydney. The nasal mask is secured to a wearer's head by a harness comprised of an upper strap and a lower strap, each of which is secured to a frame of the nasal mask. The upper portion of the frame includes a pad that engages the wearer's forehead. The frame further carries a nasal cushion that, in use of the mask, sealingly engages the wearer's nose and face. The frame also carries a mask body to which is connected a flexible conduit for the delivery of breathable gas to the mask and thereafter to an entrance to the patient's airway.

A problem with this arrangement is that the upper and lower straps are made from an elastic or resilient material which lose elasticity with time and become loose fitting about the wearer's head. Furthermore, movement of the wearer during sleep, may cause sliding movement of the straps to the point where the mask can become loose and leaks occur.

Also, the tightening of either the upper or lower strap tends to pivot the mask thereby altering the tension of the other strap making comfortable and correct adjustment difficult and time consuming.

Other harness arrangements, such as that shown in U.S. Pat. No. 5,542,128 in the name of Lomas, include an upper strap around the head and a lower strap around the neck. This arrangement exacerbates the tensioning problem discussed above as rocking of the head moves the face relative to the neck thereby altering the tension of the straps, especially the neck strap.

Another prior art arrangement is disclosed in published Australian Patent Application No. 32914/95 in the name of Buckley-Mendez.

It is important to distinguish nasal masks for the administration of CPAP treatment from respirators or breathing apparatus that are characterised by full face is cover and are intended to simultaneously deliver air to the nose and mouth of a conscious and mobile patient. In contrast, CPAP treatment primarily occurs during sleep when the wearer of a nasal mask is mostly immobile and cannot tolerate the discomfort of respirators or breathing apparatus for want of arousing from the sleep state.

The present invention is directed to overcoming, or at least ameliorating, one or more of the disadvantages of the prior art.

SUMMARY OF THE INVENTION

Accordingly, in a first aspect, the present invention provides a harness assembly for a nasal mask for communicating breathable gas to a patient's airways, the harness assembly includes a cap portion adapted to engage, in use, the occipital region of the skull, said cap portion including a connection means at each end, and a pair of upper and lower straps, each of the straps extending between one of the cap connection means and the nasal mask.

The harness assembly according to the invention grips the head in a region substantially fixed relative to the face and, as such, strap tension is not substantially affected by head movement.

Preferably, the cap connection means are adapted to allow the cap portion to pivot substantially independently of the mask and straps.

The connection means are desirably disposed, in use, adjacent the ears of the wearer. Most desirably, they are just above the ears.

The cap connection means are preferably further adapted to allow each strap to move substantially independently of the other straps.

Each strap is preferably length adjustable.

Desirably, the cap portion, in use, covers the occiput of the wearer.

In an embodiment, the cap portion engages and/or grips the curved region of the occiput.

In another embodiment, the cap portion includes an opening through which, in use, the occiput at least partially protrudes.

The connection means desirably also allows the straps to slide normally relative to the direction of the strap.

In a particularly preferred embodiment, the connection means are in the form of substantially D-shaped members. In this embodiment, the cap portion is connected to the straight portion of the D-shaped members and the upper and lower straps are each respectively connected to the upper and lower curves of the D-shaped members.

In another preferred embodiment, the connection means is in the form of a triangular member. In this embodiment, the cap ends and the upper and lower straps each respectively engage a side of the triangle.

In another particularly preferred embodiment, the connection means is in the form of a yoke shaped member having a inner bar and a pair of outer bars each angled slightly with respect to the inner bar. In this embodiment, the cap portion is connected to the inner bar and the upper and lower straps are each connected to one of the outer bars.

In yet another embodiment, the connection means are in the form of substantially "C" shaped members. In this embodiment the. lower straps connect to the head of the C, the upper straps to the middle and the cap portion to the base. In this embodiment, the cap portion and the upper straps can be manufactured from a single component The connection means is preferably produced from plastics, elastomers, composites, laminates or other like materials.

The cap portion and straps can be produced from fabric or like materials or laminates thereof. The cap portion may also be moulded to snugly fit the head, in particular to replicate the shape of the occiput, by thermoforming, fabric darting, or joining two or more pieces along a non-straight seam.

In a second aspect, the invention provides a nasal CPAP mask and harness assembly, the assembly includes a mask with a nasal cushion and mask body connected to the harness assembly of the first aspect.

BRIEF DESCRIPTION OF THE DRAWINGS

Preferred embodiments of the invention now will be described with reference to the accompanying drawings, in which.

DESCRIPTION OF THE PREFERRED EMBODIMENTS

Figure 1:
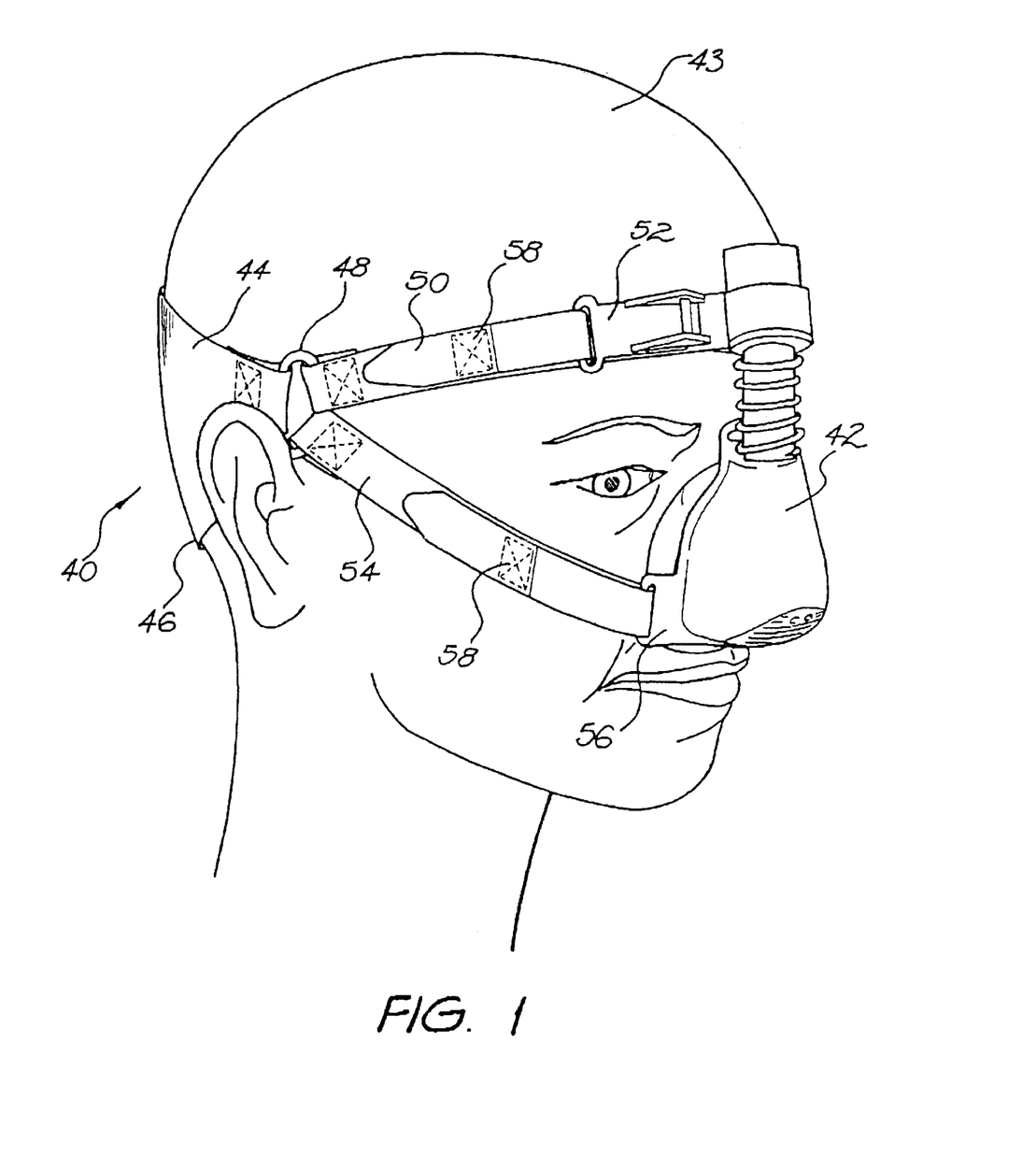
FIG. 1 is a front perspective view of a harness assembly according to a first embodiment of the invention.
Figure 2:
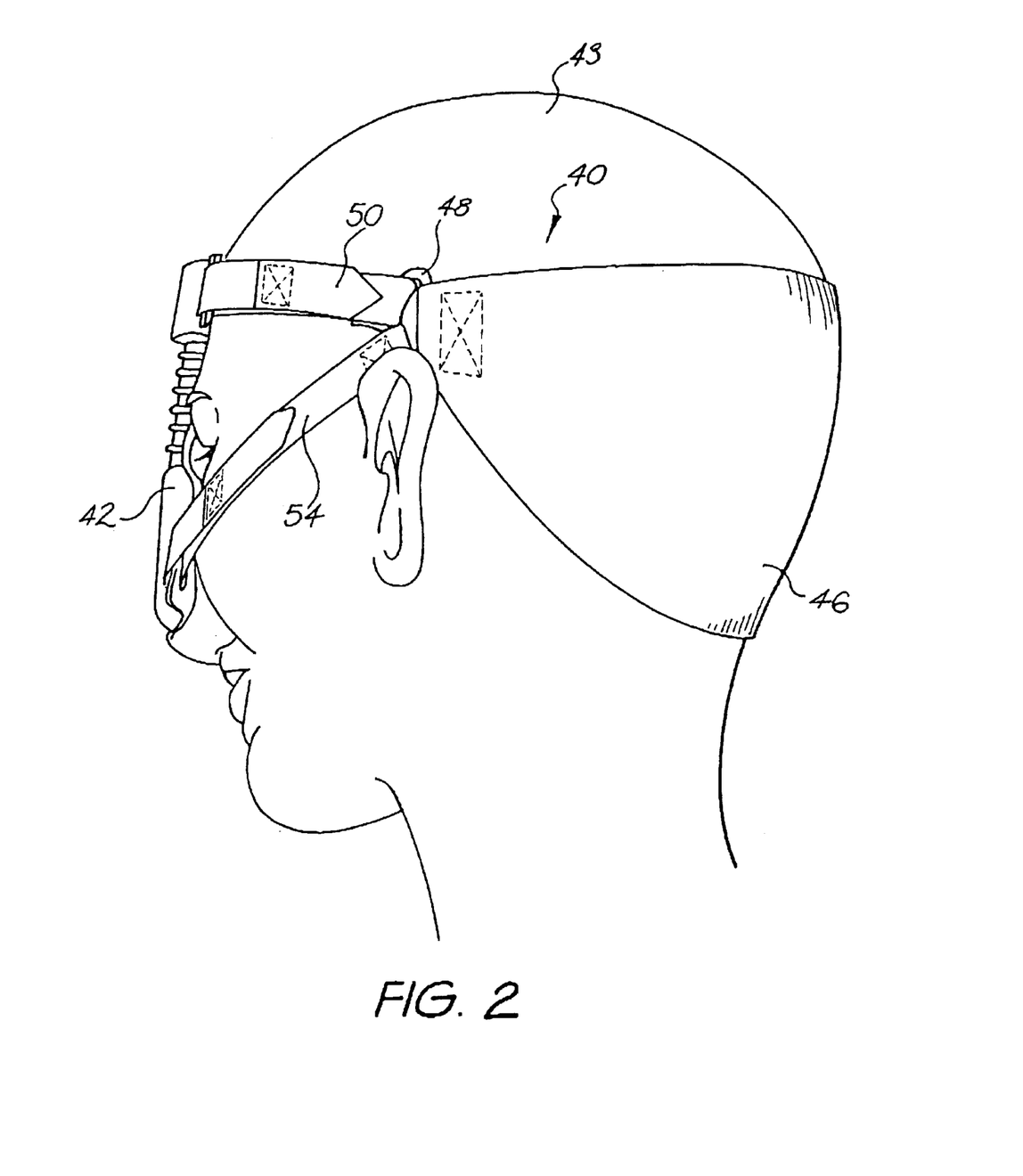
FIG. 2 is a rear perspective view of the harness assembly shown in FIG. 1.

Referring to the FIGS. 1 and 2, there is disclosed a harness assembly according to a first embodiment of the invention 40. The harness assembly 40 is. shown, in use, securing a nasal mask 42, which is suitable for CPAP treatment, to a human head 43.

The harness 40 includes a cap portion 44 which is adapted to engage the lower rear region of the wearer's skull. The cap portion 44 is substantially semi-circular in shape when laid flat. When worn, the lower most portion 46 of the cap portion 44 covers and grips the occipital region of the wearer to facilitate securely locating the cap portion during use.

The cap portion includes a connection means at each end which, in the first embodiment shown in FIG. 1 and ;is in the form of a D-shaped coupling 48. A pair of upper straps 50, of which only the left-hand is shown in FIG. 2, extend between the coupling 48 and an upper portion 52 of the nasal mask. Similarly, a pair of lower straps 54 extend between the coupling 48 and a lower portion of the mask 56

In the embodiment shown, each of the straps are length adjustable, by virtue of hook and loop connectors 58. In another embodiment, not shown, the straps are of constant length and the harness is produced in a number of sizes to suit various size heads.

The connection of the straps to the D-shaped coupling member 48 allows each of the straps 50 and 54 to pivot with respect to each other and the cap portion 44. The coupling member 48 also allows the straps and cap portion to slide slightly in a direction normal to the longitudinal direction of the strap or cap portion. As the D-shaped coupler allows the upper and lower straps and the cap portion to all move independently of one another then an improved harness is provided as movements of one of the above parts, caused by, for example, repositioning of the wearer's head during sleep, will not unduly affect the others thereby providing a more securely fitted nasal mask.

The location of the mask 42 is also unaffected when the position of cap portion 44 is independently moved for best fit.

Further, as no part of the harness assembly engages the neck, head movements, such as rocking, which alter the face to neck distance, do not affect strap tension resulting in more secure and comfortable fitting mask.

Figure 3:
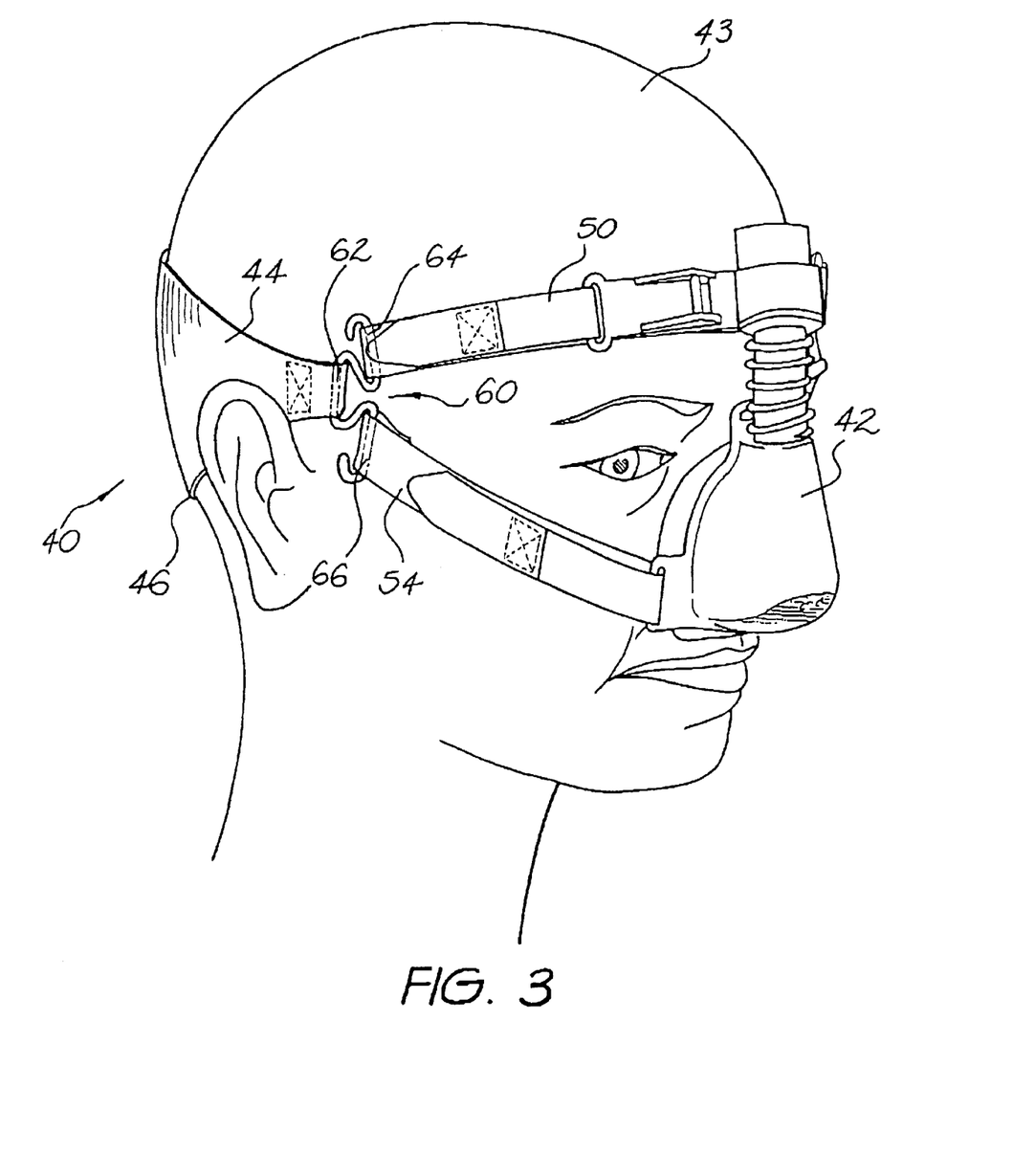
FIG. 3 is a front perspective view of a harness assembly according to a second embodiment of the invention.
Figure 4:
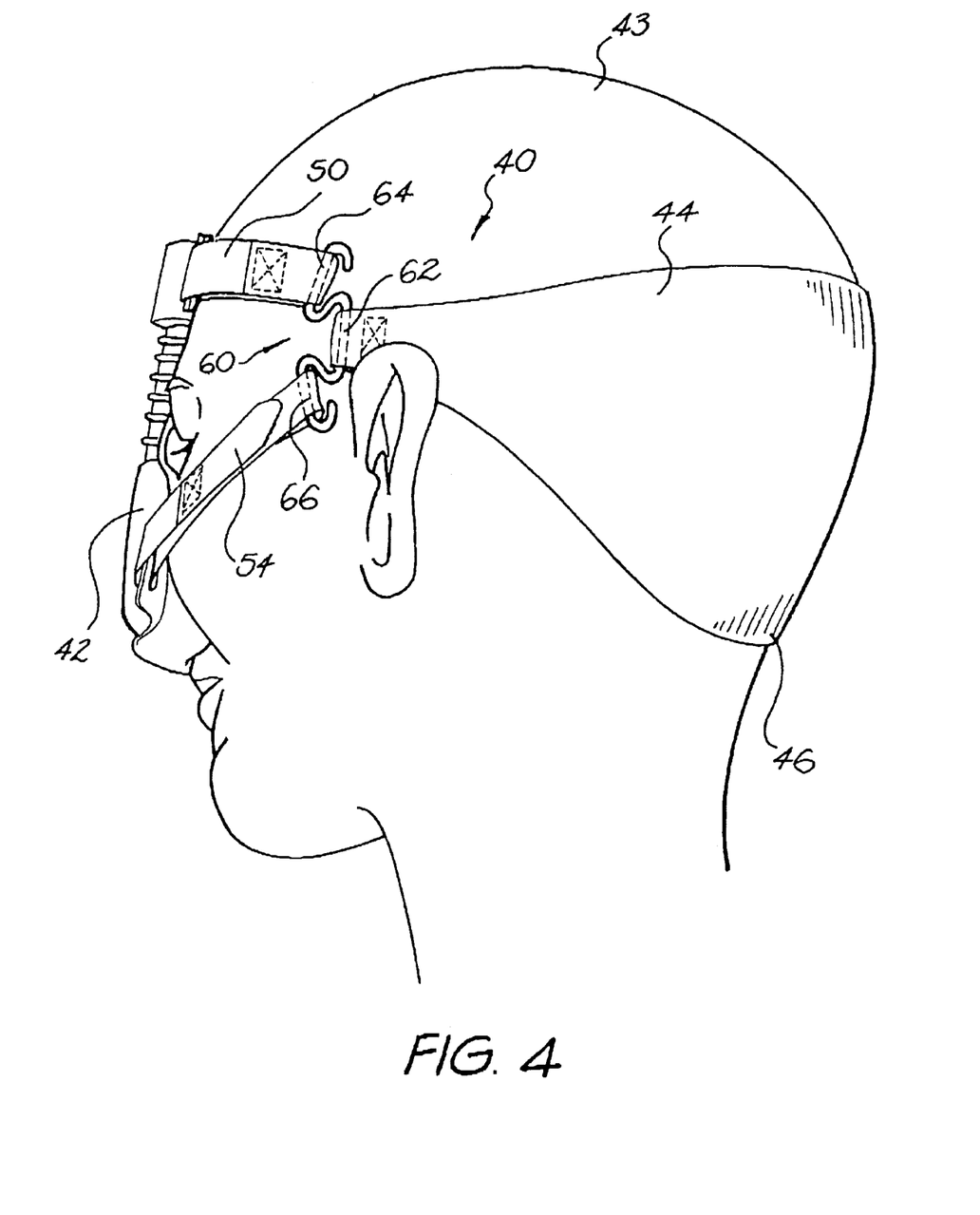
FIG. 4 is a rear perspective view of the harness assembly shown in FIG. 3.

A second embodiment of the harness assembly is shown in FIGS. 3 and 4 in which like reference numerals are used to indicate like features. In this embodiment the connection means is in the form of a yoke shaped coupling 60. The yoke 60 includes an inner bar 62 connected to an upper and lower bar 64 and 66 respectively. The upper and lower bars are angled slightly with respect to the inner bar so as to be substantially normal to the longitudinal axis of the upper and lower straps 50 and 54. Once again, the yoke 60 allows the straps 50, 54 and the cap portion 44 to move independently of one another.

Figure 5:
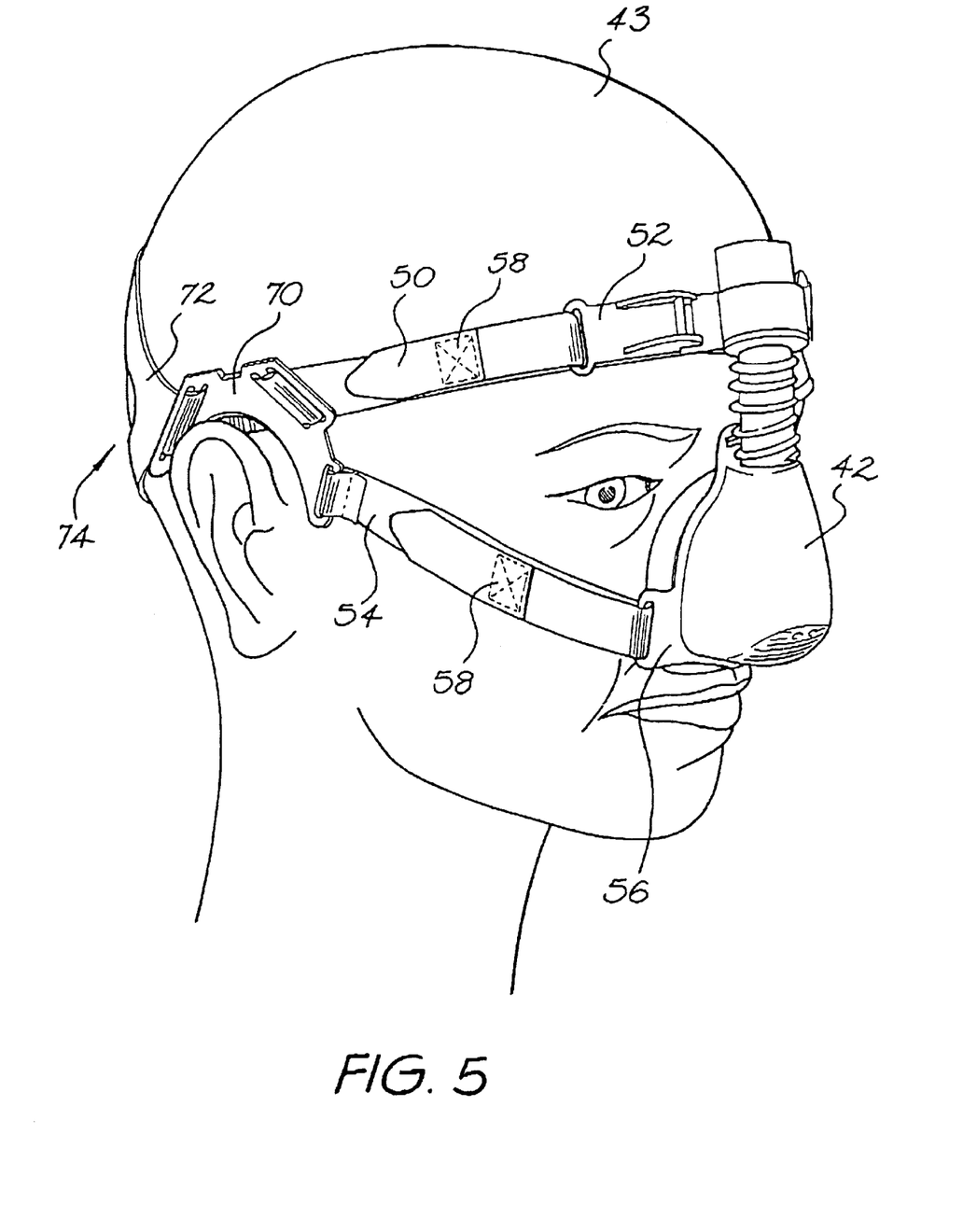
FIG. 5 is a front perspective view of a harness assembly according to a third embodiment of the invention.
Figure 6:
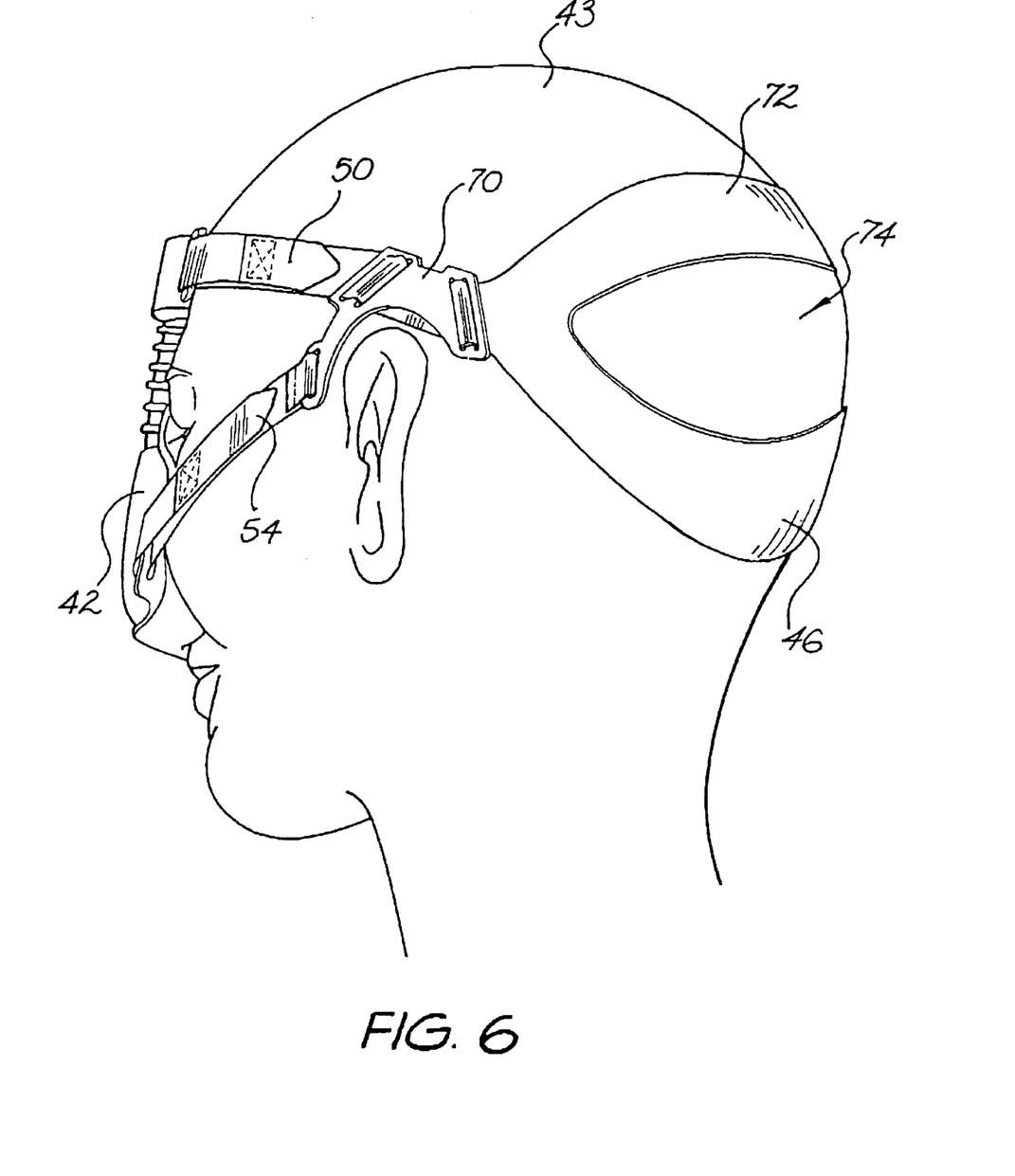
FIG. 6 is a rear view of the harness assembly shown in FIG. 5.
Figure 7:
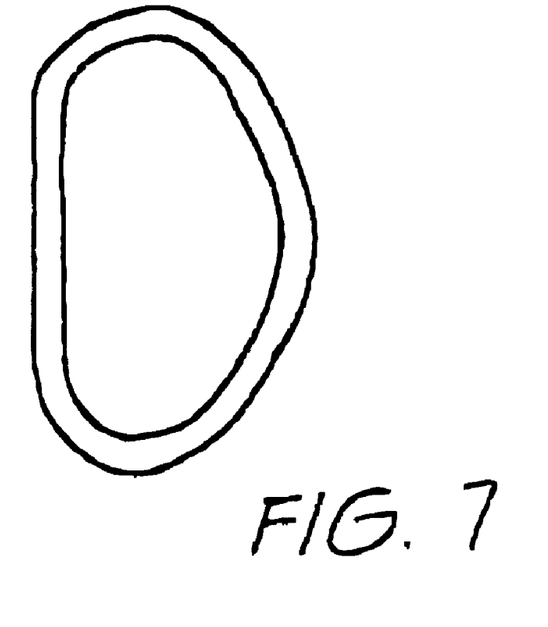
FIG. 7 is a side view of a D-shaped coupling of the first embodiment of the present invention.
Figure 8:
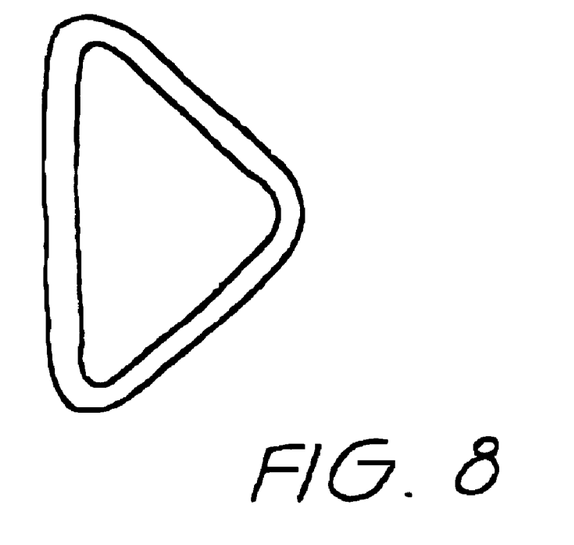
FIG. 8 is a side view of a triangular shaped coupling used in a fourth embodiment of the present invention.

A third embodiment of the harness assembly is shown in FIGS. 5 and 6. Once again, like reference numerals are used to indicate like features. In this embodiment the connection means are in the form of C-shaped members 70 disposed, in use, above the wearers ears. A cap portion 72 includes an opening 74 through which the occiput protrudes to assist in securely locating the cap portion.

The opening 74 improves the maintenance of the cap portion 72 in the correct position. Further, the opening 74 reduces heat build up under the cap portion 72, compared to these shown in FIGS. 1 to 4.

Although the invention has been described with respect to preferred embodiments, it will be appreciated by those skilled in the art, that the invention may be embodied in many other forms.

As an example, the cap portion 72 of the third embodiment may be used instead of the cap portion 44 of the first and second embodiment.

I claim:

1. A nasal mask harness assembly for securing a nasal mask to a patient's head, the harness assembly comprising:
   a cap portion adapted to engage, in use, the occipital region of the skull, said cap portion including a connector at each end; and
   a pair of upper and lower straps, each of the straps having a first end being connected to one of the cap connectors and a second end constructed and arranged to connect to the nasal mask, the connectors being constructed and arranged so as to allow the cap portion to pivot substantially independently of the mask and straps.

2. An assembly as claimed in claim 1, wherein the connectors are disposed, in use, adjacent the ears of the wearer.

3. An assembly as claimed in claim 2, wherein the connectors are disposed just above the ears.

4. An assembly as claimed in claim 1, wherein the cap connectors are adapted to allow each of the straps to move substantially independently of the other straps.

5. An assembly as claimed in claim 1, wherein each of the straps is length adjustable.

6. An assembly as claimed in claim 1, wherein the cap portion is adapted to cover the occiput of the wearer in use.

7. An assembly as claimed in claim 1, wherein the cap portion is adapted to engage the curved region of the patient's occiput.

8. An assembly as claimed in claim 1, wherein the cap portion includes an opening adapted to allow the occiput of the wearer to at least partially protrude through in use.

9. An assembly as claimed in claim 1, wherein the connectors also allow the straps to slide normally relative to the direction of the strap.

10. An assembly as claimed in claim 1, wherein the connectors are produced from plastics, elastomers, composites or laminates.

11. An assembly as claimed in claim 1, wherein the cap portion and straps are produced from fabric.

12. An assembly as claimed in claim 1, wherein the cap portion is moulded to snugly fit the head, by thermoforming, fabric darting, or joining two or more pieces along a non-straight seam.

13. An assembly as claimed in claim 12, wherein the cap portion is moulded to replicate the shape of the occiput.

14. An assembly as claimed in claim 1, wherein the cap portion is adapted to grip the curved region of the patient's occiput.

15. A nasal mask harness assembly for securing a nasal mask to a patient's head, the harness assembly comprising:
a cap portion adapted to engage, in use, the occipital region of the skull, said cap portion including a connector at each end; and
a pair of upper and lower straps, each of the straps having a first end connected to one of the cap connectors and a second end constructed and arranged to connect to the nasal mask, the connectors being constructed and arranged so as to allow the cap portion to pivot substantially independently of the mask and straps, the connectors being in the form of substantially D-shaped members.

16. An assembly as claimed in claim 15, wherein the cap portion is connected to the straight portion of the D-shaped members and the upper and lower straps are each respectively connected to the upper and lower curves of the D-shaped members.

17. A nasal mask harness assembly for securing a nasal mask to a patient's head, the harness assembly comprising:
a cap portion adapted to engage, in use, the occipital region of the skull, said cap portion including a connector at each end; and
a pair of upper and lower straps, each of the straps having a first end connected to one of the cap connectors and a second end constructed and arranged to connect to the nasal mask, the connectors being constructed and arranged so as to allow the cap portion to pivot substantially independently of the mask and straps, the connectors being in the form of triangular members.

18. An assembly as claimed in claim 17, wherein the cap ends and the upper and lower straps each respectively engage a side of the triangular member.

19. A nasal mask harness assembly for securing a nasal mask to a patient's head, the harness assembly comprising:
a cap portion adapted to engage, in use, the occipital region of the skull, said cap portion including a connector at each end; and
a pair of upper and lower straps, each of the straps having a first end connected to one of the cap connectors and a second end constructed and arranged to connect to the nasal mask, the connectors being constructed and arranged so as to allow the cap portion to pivot substantially independently of the mask and straps, the connectors being in the form of yoke shaped members each having a inner bar and a pair of outer bars for each angled slightly with respect to the inner bar.

20. An assembly as claimed in claim 19, wherein the cap portion is connected to the inner bar and the upper and lower straps are each connected to one of the outer bars.

21. A nasal mask harness assembly for securing a nasal mask to a patient's head, the harness assembly comprising:
a cap portion adapted to engage, in use, the occipital region of the skull, said cap portion including a connector at each end; and
a pair of upper and lower straps, each of the straps having a first end connected to one of the cap connectors and a second end constructed and arranged to connect to the nasal mask, the connectors being constructed and arranged so as to allow the cap portion to pivot substantially independently of the mask and straps the connectors being in the form of substantially "C" shaped members and wherein the lower straps connect to he head of the C, the upper straps to the middle and the cap portion to the base.

22. An assembly as claimed in claim 21, wherein the cap portion and the upper straps are manufactured as a single component.

23. A nasal mask and harness apparatus, the apparatus including a nasal mask for communicating breathable gas to the patient's airways connected to a harness assembly, the harness assembly comprising:
a cap portion adapted to engage, in use, the occipital region of the skull, said cap portion including a connector at each end; and
a pair of upper and lower straps, each of the straps connecting one of the cap connectors to the nasal mask, the connectors being constructed and arranged so as to allow the cap portion to pivot substantially independently of the mask and straps.

24. A method of administering CPAP treatment to a patient, said method including supplying breathable gas to the patient's airways using a nasal mask and harness apparatus, the nasal mask and harness apparatus including a nasal mask for communicating breathable gas to the patient's airways connected to a harness assembly, the harness assembly comprising:
a cap portion adapted to engage, in use, the occipital region of the skull, said cap portion including a connector at each end; and
a pair of upper and lower straps, each of the straps connecting one of the cap connectors to the nasal mask, the connectors being constructed and arranged so as to allow the cap portion to pivot substantially independently of the mask and straps.

25. A method of administering assisted respiration or mechanical ventilation to a patient, said method including supplying breathable gas to the patient's airways using a nasal mask and harness apparatus, the nasal mask and harness apparatus including a nasal mask for communicating breathable gas to the patient's airways connected to a harness assembly, the harness assembly comprising:
a cap portion adapted to engage, in use, the occipital region of the skull, said cap portion including a connector at each end; and
a pair of upper and lower straps, each of the straps connecting one of the cap connectors to the nasal mask, the connectors being constructed and arranged so as to allow the cap portion to pivot substantially independently of the mask and straps.

* * * * *